US00PP32774P3

(12) United States Plant Patent
van Sambeek

(10) Patent No.: US PP32,774 P3
(45) Date of Patent: Jan. 26, 2021

(54) ***LEUCANTHEMUM* PLANT NAMED 'DOLEUCSWEDABIR'**

(50) Latin Name: *Leucanthemum maximum*
Varietal Denomination: Doleucswedabir

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,820

(22) Filed: Jun. 11, 2019

(65) Prior Publication Data

US 2020/0396882 P1 Dec. 17, 2020

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285, 263.1, 284, 286
CPC . A01H 5/02; A01H 5/025; A01H 5/00; A01H 6/14
See application file for complete search history.

(56) References Cited

PUBLICATIONS

Gro 'N Sell Quality Starter Plants Elements for your Success 2018-20109, retrieved on Mar. 18, 2020, retrieved from the Internet at http://gronsell.com/wp-content/uploads/2018/08/GNS_2019_FINAL-web.pdf, 2 cover pages, pp. 1-2,29,44. (Year: 2019).*

Pilon. GrowerTalk Green Profit More Great Perennials from Spring Trials and PPA's Symposium Sneak Peak 2018, retrieved on Mar. 18, 2020, retrieved from the Internet at https://www.growertalks.com/Newsletters/View/?article=2541, 8 pp. (Year: 2018).*

* cited by examiner

*Primary Examiner* — June Hwu
(74) *Attorney, Agent, or Firm* — C. A. Whealy

(57) ABSTRACT

A new and distinct cultivar of *Leucanthemum* plant named 'Doleucswedabir', characterized by its upright and mounded plant habit; freely branching habit; strong and upright flowering stems; early and freely flowering habit; large inflorescences with white-colored ray florets and large central disc; and good garden performance.

1 Drawing Sheet

Botanical designation: *Leucanthemum maximum.*
Cultivar denomination: 'DOLEUCSWEDABIR'.

BACKGROUND OF THE INVENTION

The present invention relates to a new and distinct cultivar of *Leucanthemum* plant, botanically known as *Leucanthemum maximum* and hereinafter referred to by the name 'Doleucswedabir'.

The new *Leucanthemum* plant is a product of a planned breeding program conducted by the Inventor in Aalsmeer, The Netherlands. The objective of the breeding program is to create new *Leucanthemum* plants with numerous attractive inflorescences.

The new *Leucanthemum* plant originated from an open-pollination in June, 2013 of a proprietary selection of *Leucanthemum maximum* identified as code number LC-0010, not patented, as the female, or seed, parent with an unknown selection of *Leucanthemum maximum* as the male, or pollen, parent. The new *Leucanthemum* plant was discovered and selected by the Inventor as a single flowering plant from within the progeny of the stated open-pollination in a controlled environment in Aalsmeer, The Netherlands in April, 2014.

Asexual reproduction of the new *Leucanthemum* plant by vegetative terminal cuttings in Aalsmeer, The Netherlands, since May, 2014 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doleucswedabir'. These characteristics in combination distinguish 'Doleucswedabir' as a new and distinct *Leucanthemum* plant:

1. Upright and mounded plant habit.
2. Freely branching habit.
3. Strong and upright flowering stems.
4. Early and freely flowering habit.
5. Large inflorescences with white-colored ray florets and large central disc.
6. Good garden performance.

Plants of the new *Leucanthemum* differ primarily from plants of the female parent selection in the following characteristics:

1. Plants of the new *Leucanthemum* are more freely branching than plants of the female parent selection.

2. Plants of the new *Leucanthemum* are more freely flowering than plants of the female parent selection.

Plants of the new *Leucanthemum* can be compared to plants of *Leucanthemum* x *superbum* 'Victorian Secret', disclosed in U.S. Plant Pat. No. 22,654. In side-by-side comparisons, plants of the new *Leucanthemum* differ from plants of 'Victorian Secret' in the following characteristics:

1. Plants of the new *Leucanthemum* are more freely branching than plants of 'Victorian Secret'.
2. Plants of the new *Leucanthemum* have broader and darker green-colored leaves than plants of 'Victorian Secret'.
3. Plants of the new *Leucanthemum* have smaller inflorescences than plants of 'Victorian Secret'.
4. Plants of the new *Leucanthemum* are more freely flowering than plants of 'Victorian Secret'.
5. Inflorescences of plants of the new *Leucanthemum* have fewer ray florets and more disc florets than inflorescences of plants of 'Victorian Secret'.

BRIEF DESCRIPTION OF THE PHOTOGRAPH

The accompanying colored photograph illustrates the overall appearance of the new *Leucanthemum* plant showing the colors as true as it is reasonably possible to obtain in colored reproductions of this type. Colors in the photograph may differ slightly from the color values cited in the detailed botanical description which accurately describe the colors of the new *Leucanthemum* plant. The photograph is a close-up view of a typical flowering plant of 'Doleucswedabir' grown in a container.

DETAILED BOTANICAL DESCRIPTION

The aforementioned photograph and following observations and measurements describe plants grown in 13-cm containers during the spring in a glass-covered greenhouse in Aalsmeer, The Netherlands and under cultural practices typical of commercial *Leucanthemum* production. During the production of the plants, day temperatures averaged 20° C. and night temperatures averaged 8° C. Plants were pinched one time one week after planting and were three months old when the photograph was taken and four months old when the description was taken. In the following description, color references are made to The Royal Horticultural Society Colour Chart, 2007 Edition, except where general terms of ordinary dictionary significance are used.

Botanical classification: *Leucanthemum maximum* 'Doleucswedabir'.

Parentage:

*Female, or seed, parent*.—Proprietary selection of *Leucanthemum maximum* identified as code number LC-0010, not patented.

*Male, or pollen, parent*.—Unknown selection of *Leucanthemum maximum*, not patented.

Propagation:

*Type*.—Terminal vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white to light brown in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; upright and mounded plant habit; vigorous growth habit; moderate growth rate; freely branching habit with about eight to ten primary branches each with about five to seven secondary branches developing per plant.

*Plant height*.—About 40 cm to 50 cm.

*Plant width*.—About 45 cm.

*Branch description*.—Length: About 15 cm. Diameter: About 5 mm. Internode length: About 2 cm to 3 cm. Strength: Strong. Aspect: Erect to about 30° from vertical. Texture and luster: Sparsely pubescent; semi-glossy. Color: Close to 137C.

*Leaf description*.—Arrangement: Alternate; simple; sessile. Length: About 15 cm. Width: About 2.5 cm to 5.5 cm. Shape: Spatulate to oblong. Apex: Acute to apiculate. Base: Attenuate. Margin: Serrate. Texture and luster, upper and lower surfaces: Pubescent; matte. Venation pattern: Prominent midvein; reticulate. Color: Developing leaves, upper surface: Close to 137A. Developing leaves, lower surface: Close to 137C. Fully developed leaves, upper surface: Darker than 137A; venation, close to 145B. Fully developed leaves, lower surface: Close to 137C; venation, close to 145B.

Inflorescence description:

*Appearance*.—Large inflorescences with oblanceolate-shaped ray florets and tubular disc florets; inflorescences held upright on strong peduncles, inflorescences face mostly upright; ray and disc florets develop acropetally on a capitulum.

*Fragrance*.—Slightly fragrant, pleasant.

*Flowering response*.—Plants begin flowering about twelve weeks after planting; plants flower naturally during June and July in The Netherlands.

*Postproduction longevity*.—Inflorescences maintain good substance for about six weeks on the plant; inflorescences persistent.

*Quantity of inflorescences*.—Freely flowering habit, about 32 inflorescences develop per plant during the flowering season.

*Inflorescence size*.—Diameter: About 9 cm. Depth (height): About 1 cm. Disc diameter: About 2 cm.

*Receptacles*.—Height: About 6 mm. Diameter: About 1.4 cm. Color: Close to 145B.

*Inflorescence buds*.—Height: About 4 mm. Diameter: About 1 cm. Shape: Flattened sphere. Color: Close to 137D.

*Ray florets*.—Quantity per inflorescence: About 34 arranged in a single whorl. Length: About 3.5 cm. Width: About 8mm. Shape: Oblanceolate. Apex: Rounded and shallowly emarginate. Base: Attenuate. Margin: Entire; distally, slightly undulate. Aspect: Mostly horizontal to reflexing. Texture and luster, upper and lower surfaces: Smooth, glabrous; matte. Color: When opening and fully opened, upper surface: Close to 155D; color does not change with development. When opening and fully opened, lower surface: Close to 155D; color does not change with development.

*Trans florets*.—Appearance and quantity: Interior to the ray florets and surrounding the disc are about three to four whorls each with about 27 trans florets with acute apices. Length: About 1.2 cm. Width: About 2 mm. Texture and luster, upper and lower surfaces: Smooth, glabrous; matte. Color: When opening and fully opened, upper surface: Close to 155D; color does not change with development. When opening and fully opened, lower surface: Close to 155D; color does not change with development.

*Disc florets*.—Quantity per inflorescence: About 400 massed at the center of the receptacle arranged in about 14 whorls. Length: About 8 mm. Diameter: About 1 mm. Shape: Fused tubular. Apex: Acute, five-pointed. Texture and luster, inner and outer surfaces: Smooth, glabrous; slightly glossy. Color: When opening and fully opened, inner surface: Close to 12A; color does not change with development. When opening and fully opened, outer surface: Close to 144D; color does not change with development.

*Involucral bracts*.—Quantity per inflorescence: About 58 arranged in about three whorls. Length: About 8 mm. Width: About 3 mm. Shape: Oblong. Apex: Obtuse. Base: Fused. Margin: Entire, membraneous. Texture and luster, upper and lower surfaces: Smooth, glabrous; somewhat glossy. Color, upper and lower surfaces: Close to 138A.

*Peduncles*.—Length: About 40 cm to 50 cm. Diameter: About 6 mm. Strength: Strong. Aspect: Upright to about 30° from vertical. Texture and luster: Slightly pubescent; matte. Color: Close to 137C.

*Reproductive organs*.—Androecium: Present on disc florets only. Quantity per floret: Five per disc floret. Filament length: About 1 mm. Filament color: Close to 145C. Anther shape: Roughly rectangular. Anther length: About 1.5 mm. Anther color: Close to 15A. Pollen amount: Abundant. Pollen color: Close to 17A. Gynoecium: Present on ray, trans and disc florets. Quantity per floret: One. Pistil length: About 4.5 mm. Stigma diameter: Close to 1 mm. Stigma shape: Bi-parted. Stigma color: Close to 12B. Style length: About 4 mm. Style color: Close to 154C. Ovary color: Close to 145C.

*Seeds and fruits*.—To date, seed and fruit development have not been observed on plants of the new *Leucanthemum*.

Pathogen & pest resistance: To date, plants of the new *Leucanthemum* have not been observed to be resistant to pathogens and pests common to *Leucanthemum* plants.

Garden performance: Plants of the new *Leucanthemum* have been observed to have good garden performance and to tolerate wind and rain, to tolerate temperatures ranging from −15° C. to 35° C.

It is claimed:

1. A new and distinct *Leucanthemum* plant named 'Doleucswedabir' as illustrated and described.

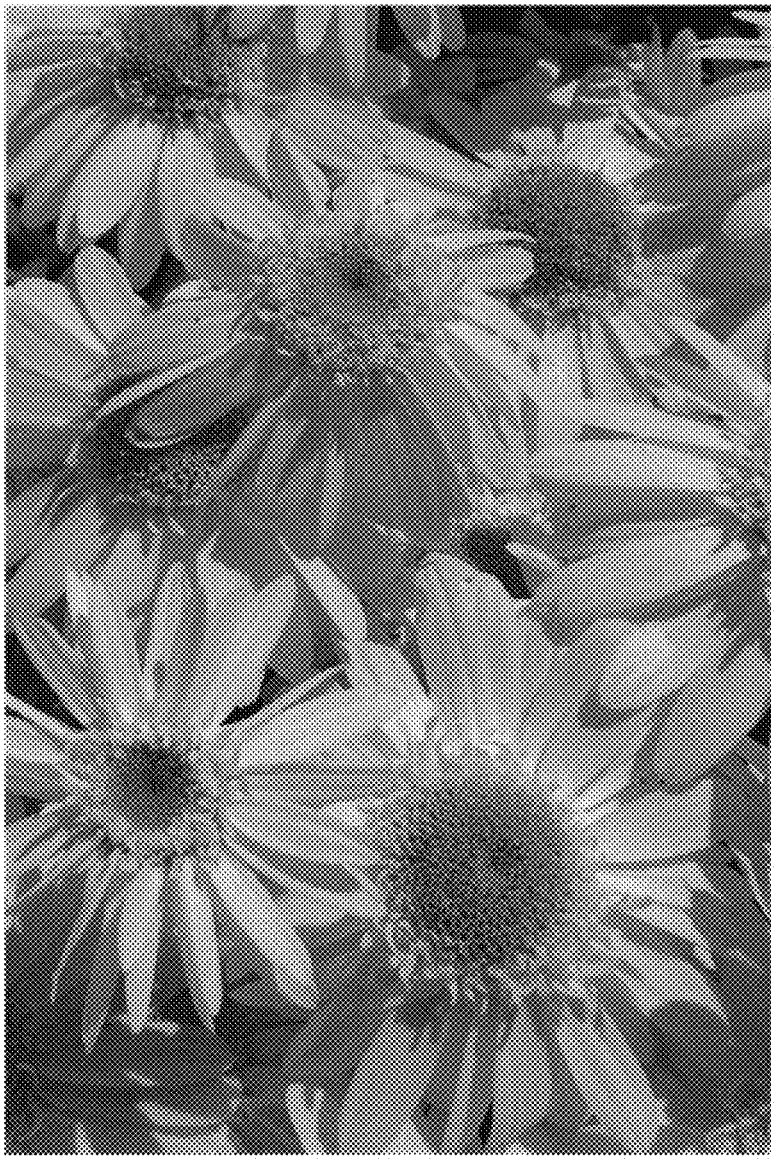

* * * * *